United States Patent
Fleming

(10) Patent No.: US 11,202,800 B1
(45) Date of Patent: Dec. 21, 2021

(54) METHODS FOR TREATING EMOTIONAL COGNITIVE DISCONNECT

(71) Applicant: Jeanne Fleming, Longview, WA (US)

(72) Inventor: Jeanne Fleming, Longview, WA (US)

(*) Notice: Subject to any disclaimer, the term of this patent is extended or adjusted under 35 U.S.C. 154(b) by 0 days.

(21) Appl. No.: 16/504,028

(22) Filed: Jul. 5, 2019

Related U.S. Application Data

(63) Continuation of application No. 14/922,742, filed on Oct. 26, 2015, now abandoned, and a continuation-in-part of application No. 14/189,898, filed on Feb. 25, 2014, now abandoned, and a continuation-in-part of application No. 14/189,878, filed on Feb. 25, 2014, now abandoned, and a continuation-in-part of application No. 14/189,916, filed on Feb. 25, 2014, now abandoned.

(60) Provisional application No. 61/769,607, filed on Feb. 26, 2013, provisional application No. 61/888,081, filed on Oct. 8, 2013, provisional application No. 61/896,847, filed on Oct. 29, 2013.

(51) Int. Cl.
| | |
|---|---|
| *A61K 33/06* | (2006.01) |
| *A61K 31/19* | (2006.01) |
| *A61K 31/047* | (2006.01) |
| *A61K 33/30* | (2006.01) |

(52) U.S. Cl.
CPC ............ *A61K 33/06* (2013.01); *A61K 31/047* (2013.01); *A61K 31/19* (2013.01); *A61K 33/30* (2013.01)

(58) Field of Classification Search
None
See application file for complete search history.

(56) References Cited

U.S. PATENT DOCUMENTS

| | | | | |
|---|---|---|---|---|
| 2002/0182196 A1* | 12/2002 | McCleary | .............. | A61K 31/00 424/94.1 |
| 2008/0317883 A1* | 12/2008 | Choi | ...................... | A61K 45/06 424/730 |
| 2011/0159048 A1* | 6/2011 | Crain | ................... | A61K 31/439 424/400 |

OTHER PUBLICATIONS

Yary et al., Dietary Magnesium may modulate depression, Biological Trace Element Research, (Dec. 2012 available online), vol. 151, Issue 3, pp. 324-329 (Year: 2012).*

* cited by examiner

*Primary Examiner* — David J Blanchard
*Assistant Examiner* — Sarah J Chickos
(74) *Attorney, Agent, or Firm* — McCoy Russell LLP

(57) ABSTRACT

The present invention relates to the treatment of refractory Emotional Cognitive Disconnect (ECD) through a combination of pharmaceutical agents and therapy. Individual patients are treated with a combination of magnesium, inositol, and N-acetylcysteine along with Vitamin E, Vitamin C, zinc, biotin, alphalipoic acid and lysine as required. The compositions may be administered sequentially or simultaneously in any order and may be formulated in singular or combinatorial dosage forms.

14 Claims, No Drawings

METHODS FOR TREATING EMOTIONAL COGNITIVE DISCONNECT

CROSS-REFERENCE TO RELATED APPLICATIONS

Cross Reference to Related Application

The present application is a continuation of U.S. patent application Ser. No. 14/922,742, filed on Oct. 26, 2015. U.S. patent application Ser. No. 14/922,742 is a continuation-in-part application of U.S. patent application Ser. No. 14/189,878, filed on Feb. 25, 2014, U.S. patent application Ser. No. 14/189,898, filed on Feb. 25, 2014, and U.S. patent application Ser. No. 14/189,916, filed on February 25, 2014. U.S. Patent Application No. 14/189,916 also claims benefit of U.S. Provisional Application No. 61/769,607, filed on Feb. 26, 2013, U.S. Provisional Application No. 61/888,081, filed on Oct. 8, 2013, and U.S. Provisional Application No. 61/896,847, filed on Oct. 29, 2013. U.S. patent application Ser. No. 14/189,878 also claims priority to U.S. Provisional Application No. 61/769,607, filed on Feb. 26, 2013, U.S. Provisional Application No. 61/888,081, filed on Oct. 8, 2013, and U.S. Provisional Application No. 61/896,847, filed on Oct. 29, 2013. U.S. patent application Ser. No. 14/189,898 also claims priority to U.S. Provisional Application No. 61/769,607, filed on Feb. 26, 2013, U.S. Provisional Application No. 61/888,081, filed on Oct. 8, 2013, and U.S. Provisional Application No. 61/896,847, filed on Oct. 29, 2013. The entire contents of each of the above-identified applications are incorporated herein by reference for all purposes.

FIELD OF THE INVENTION

The present invention relates to treatment protocols for emotional cognitive disconnect.

BACKGROUND

Throughout the past thirty years much progress has been made in the field of psychology in the diagnosis and treatment of anxiety disorders as sequenced with and differentiated from depressive disorders as well as specifically dissociative disorders and phenomena. Emotional Cognitive Disconnect (ECD) results from incomplete emotional processing, from one incident, or several, almost always negative overwhelm, always intense either singly or the accumulation, which results in one or more of the following indicators: experiencing guilt that is unrealistic; worrying excessively, also unrealistic; telling stories about long past events, with a large amount of negative emotion still present; telling stories about long past events in a compartmentalized way, rather than a sequential way reflecting all parts of the story that have been consolidated; lack of normal emotional feelings when experiencing or recounting current events; reacting to current life experience in an overly cognitive way; reacting to current life experience in an overly negative, emotional way; reacting to people or experiences with too much personalization or internalization; current life experiences overly activate the sympathetic nervous system, instead of the parasympathetic system, and does not reset back when possible, as the norm; seeing one's own self in an overly negative way, does not see or own positives; seeing others in an overly negative way, does not see or believe positives; sees own self in an overly and unrealistic positive way, does not see any negatives; sees others in an overly positive way, does not see negatives; difficulty languaging events accurately in a way that describes them without re-enacting them or putting the feelings about them onto others; and with emerging dementias, various difficulties with memory, motor skills, emotion and behavior and life functioning.

Any time there has been a chronic anxiety disorder or process, with increased life responsibility and stressors, eventually at least a mild secondary depression will emerge, which will obscure the anxiety signs and symptoms. At that point, treating the depression while observing for any anxiety as the depression recedes is vital. Once anxiety is the presenting factor, lowering the over-all anxiety level assumes first priority, since any other signs and symptoms will have a lower anxiety baseline from which to activate, is next most important. That might be enough intervention to control both the over-all anxiety as well as specific signs and symptoms, such as Panic Disorder or reactions, phobic reactions, as well as begin to differentiate and arrest (if present) emerging dementias, especially Alzheimer's.

When emotions, cognitive thought, and word labels match, the brain synchronizes them automatically, utilizing the parasympathetic nervous system and a cascade regulatory feedback mechanism such that the Emotional Cognitive Connections (ECC) move through and the biochemicals stimulated by the emotion are metabolized and broken down with the experience moving from short term memory processing capacity to long term memory such that when there is recall, raw, unprocessed emotion is no longer present.

When emotions, cognitive thought, and word labels do not match due to a high intensity experience or emotional reaction, the sympathetic nervous system instead of the parasympathetic nervous system is employed resulting in Emotional Cognitive Disconnect (ECD) where dendrite-axon steps are missed and accelerated emotions override the ability of the brain to keep up with matching thought and words.

Generally, ECD is treated by putting a patient on a currently available medication such as pregabalin, gabapentin, or duloxetine to reduce levels of initial distress, reduce depressive signs and symptoms, anxiety, guilt and over-concern with others. This process is slow and time consuming taking up to three months to accomplish, making sure that the signs and symptoms have been correctly identified and categorized, tolerance of the drug, and a positive effect of the drug. Once drug tolerance and efficacy have been established, then the dose requirement is determined to increase functioning and positiveness. However, such treatments do not work for every patient. There is therefore an unmet need for treating patients who have treatment-resistant ECD.

BRIEF SUMMARY

Provided herein are methods for treating refractory emotional cognitive disconnect (ECD). In some embodiments, treatment of refractory ECD may be through inhibition of voltage dependent calcium channels. In other embodiments, treatment of refractory ECD may be accomplished through the restoration of parasympathetic functioning. In further embodiments, treatment of refractory ECD may be accomplished through the stabilizing of synaptic processing capacity and/or the lengthening of synaptic sequences.

Individuals may be diagnosed with refractory ECD by any means generally used by those of skill in the art. In some embodiments, secondary diagnosis may occur through the use of clinical scales such as, but not limited to, the Beck Depression Inventory or the Cage Questionnaire for the testing of Opioid Dependence of Sexual Abuse Victims with Chronic Pain. In other embodiments, diagnosis may occur through clinical observation including observation of, but not limited to, (1) the defined separation of affect/emotion and cognition based on each individual; (2) the inability to self-observe the separation and account for it; (3) the inability to combine the various affects and cognitions by the individual; (4) the repeated inability of the individual to listen when affect/emotion and cognitions were combined by someone else; (5) the level of difficulty that the separate reactions caused in the individuals lives, both historically and current; and (6) the inability to not only combine what others combine easily and without obvious effort, followed by the subsequent inability to learn from past experiences in order to make the present and future different; (7) the inability to problem-solve and plan in sequential steps; (8) when combinations occurred, with great difficulty and much time delays, and repeated efforts, with someone else's assistance, with an initial cognitive and emotional reaction of positive, immediately followed by self-doubt, self-criticism, self-recrimination, that is, once Emotion and Cognition Connect (ECC) occurred, then negative thoughts and feelings were a result, rather than sustained positives; (9) Panic Disorder; (10) Panic Attacks; (11) some Phobic Reactions; and finally, (12) the beginning stages of some dementias, especially Alzheimer's. In further embodiments, diagnosis may be determined through patient complaints or family observations of problems with depression, anxiety, flashbacks, reenactments, self-sabotage as well as medical problems such as, but not limited to, headaches, stomachaches, muscle tenseness, difficulty with self-care behaviors, chronic pain, chronic back pain, or other indicators known to those of skill in the art. In additional embodiments, diagnosis of ECD may occur through a combination of one or more of clinical scales, clinical observation, patient complaints and family observations.

Individuals diagnosed with ECD may be treated using a combination of pharmaceutical agents, clinical observations and therapy. For example, individuals may be administered a first composition comprising about 250 mg of magnesium daily for an initial period of about four to about eight weeks. The individual patient may meet weekly with a therapist or other mental health professional for about four to about eight weeks for assessment of tolerance to the magnesium and/or increased emotional processing. In some embodiments, tolerance to the first composition is determined by an absence or tolerable occurrence of stomach upset, nausea, vomiting, or diarrhea. If at the end of about 4 to about 8 weeks (a first and second month), it is determined by the mental health professional and/or the individual patient that additional remediation is needed, the individual patient may additionally be administered a second composition comprising about 250 mg of inositol in conjunction with the first composition while continuing weekly meetings with a mental health professional. The inositol and magnesium may be administered simultaneously or sequentially in either order at the same or different times of day. In some embodiments, the first and second composition may be combined in a single pharmaceutical composition. The amount of inositol in the second composition may be increased by up to about 250 mg per day for 24 weeks (a third, fourth, fifth, sixth, seventh and eighth month), for a total of 18000 mg per day. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium and inositol combination. Tolerance to inositol may be characterized by an absence or tolerable amount of nausea, tiredness, headache, and dizziness.

If it is determined that further additional treatment is needed, the individual patient may further be administered a third composition comprising about 500 to about 1000 mg of N-acetylcysteine per day in combination with the first and second composition for a ninth, tenth, eleventh and/or twelfth month or earlier in the treatment cycle such as at the fourth, fifth, sixth, seventh or eighth month or any subset thereof. Tolerance of N-acetylcysteine is determined by an absence or tolerable level of nausea, vomiting, and diarrhea or constipation. Additionally, if mutually decided by all pertinent practitioners/providers and the patient, the individual patient may take a fourth composition comprising about 50 mg per day of zinc. The combination of the first, second, third and fourth compositions may be continued for a total of 24 months counting from the first administration of the first composition. The first, second, third and fourth compositions may be administered simultaneously or sequentially in either order at the same or different times of day. In some embodiments, the one or more of the first, second, third and fourth compositions may be combined in a single pharmaceutical composition. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium, inositol, and N-acetylcysteine and zinc combination.

In some embodiments, an individual diagnosed with refractory ECD may be treated through the inhibition of voltage dependent calcium channel antagonists through the administration of one or more voltage dependent calcium channel antagonists. For example, individuals may be administered a first composition comprising a first voltage dependent calcium channel agonist such as about 250 mg of magnesium daily. The individual may meet weekly with a therapist or other mental health professional for about four to about eight weeks for assessment of tolerance to the magnesium and/or increased emotional processing. In some embodiments, tolerance to the first composition is determined by an absence or tolerable level of stomach upset, nausea, vomiting, or diarrhea. If at the end of about four to about eight weeks (a first and second month), it is determined by the mental health professional and/or the individual patient that additional remediation is needed, the individual patient may additionally be administered a second voltage dependent calcium channel antagonist such as a second composition comprising about 250 mg of inositol in conjunction with the first composition. The inositol and magnesium may be administered simultaneously or sequentially in either order at the same or different times of day. In some embodiments, the first and second composition may be combined in a single pharmaceutical composition. The amount of inositol in the second composition may be increased by up to about 250 mg per day for 24 weeks (a third, fourth, fifth, sixth, seventh and eighth month) for a total of 18000 mg per day. Tolerance to inositol may be characterized by an absence or tolerable amount of nausea, tiredness, headache, and dizziness. In some embodiments the addition of a second calcium channel antagonist such as inositol may be at an earlier time point such as at the beginning of the second month of treatment counting from the beginning of the administration of magnesium. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium and inositol combination. If it is determined that additional treatment is needed, the individual patient may further be administered a third composition comprising about 500 to about 1000 mg of N-acetylcysteine per day in combination with the first and second composition for a ninth, tenth, eleventh and/or twelfth month or earlier in the course of treatment such as starting at the sixth month from the initial does of magnesium. Tolerance of N-acetylcysteine is determined by an absence or tolerable level of nausea, vomiting, and diarrhea or constipation. Additionally, if mutually decided by all pertinent practitioners/providers and the patient, the individual patient may take a fourth composition comprising about 50 mg per day of zinc. The combination of the first, second, third and fourth compositions may be continued for a total of 24 months counting from the first administration of the first composition. The first, second, third and fourth compositions may be administered simultaneously or sequentially in either order at the same or different times of day. In some embodiments, the one or more of the first, second, third and fourth compositions may be combined in a single pharmaceutical composition. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium, inositol, N-acetylcysteine combination and zinc combination.

ECD triggers an imbalance between sympathetic and parasympathetic functioning. Treatment of ECD may involve regulation and control of voltage dependent calcium channels (VDCCs) that activate the sympathetic nervous system in the optimal band activated area (another source cites the hypothalamus as the pertinent location-perhaps the optimal band is in the hypothalamus) which moves the body's own transmission sequencing from parasympathetic (daily, energy-conserving pathways) to sympathetic (energy-expending pathways) which has multiple short and long term deleterious effects within the body, if over-utilized, or the body fails to re-set itself back to parasympathetic. Sympathetic pathways work well using adrenaline and related biochemicals to activate energy; however, it compromises in negative ways the immune system and several other systems. It can become particularly complicated if a major bereavement process gets activated while the body is already operating sympathetically. Each new, unresolved stressor adds to the imbalances. In some embodiments, a method of restoring parasympathetic functioning may include identifying an individual suffering from emotional cognitive disconnect; administering daily to the individual in need of restoration a first composition; evaluating the individual weekly for tolerance of the first composition; monitoring the individual weekly for increased parasympathetic functioning; determining tolerance for the first composition; and/or while continuing administration of the first composition, administering daily a second composition. In some embodiments, the first composition may include about 250 mg of magnesium. In further embodiments, the second composition may comprise inositol. The inositol may start at a dose of 250 mg and be increased daily to a total of 18000 mg. Tolerance to inositol may be characterized by an absence or tolerable amount of nausea, tiredness, headache, and dizziness. If it is determined by a mental health practitioner in combination with the patient that further treatment is necessary. In some embodiments, daily administration of a third composition comprising about 500 mg to about 1000 mg per day of N-acetylcysteine may be taken in combination with the first composition and the second composition for a fifth and sixth month and/or a ninth and tenth month. Tolerance of N-acetylcysteine is determined by an absence or tolerable level of nausea, vomiting, and diarrhea or constipation. In additional embodiments, treatment may further include a fourth composition comprising about 50 mg of zinc. Such treatment may continue for up to about 24 months. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium, inositol, N-acetylcysteine and zinc combination.

Increased parasympathetic functioning may be evaluated by any method known to those of skill in the art. In some embodiments, parasympathetic functioning may be evaluated using one or more methods, including, but not limited to, a Valsalva maneuver, respiratory arrhythmia, isometric handgrip test, cold pressor test, mental arithmetic, orthostatic test, mental arithmetic test, head up tilt test, baroreflex sensitivity testing, analysis of heart rate variability, measurements of noradrenaline concentration, microneurography, thermoregulatory sweat test, sympathetic skin response and quantitative sudomotor axon reflex test. In other embodiments, parasympathetic functioning may be evaluated through clinical observation. In further embodiments, parasympathetic functioning may be evaluated using a clinical scale such as, but not limited to, the Beck Depression Inventory, or the Cage Questionnaire for the testing of Opioid Dependence of Sexual Abuse Victims with Chronic Pain both of which imply ECD clinically. In additional embodiments, parasympathetic functioning may be evaluated using one or more of the tests, observations, and/or clinical scales alone or in combination.

In yet another embodiment, individuals with ECD may be treated by inhibiting calmodulin dependent phosphorylation of synapsin I. Such individuals may be administered a first composition comprising about 250 mg of magnesium daily for about four to eight weeks. The individual may meet weekly with a therapist or other mental health professional for about four to about eight weeks for assessment of tolerance to the magnesium and/or increased emotional processing. In some embodiments, tolerance to the first composition is determined by an absence, and/or tolerable amount, of stomach upset, nausea, vomiting, or diarrhea. If at the end of about 4 to about 8 weeks (a first and second month), it is determined by the mental health professional and/or the individual patient that additional remediation is needed, the individual patient may additionally be administered a second voltage dependent calcium channel antagonist comprising about 250 mg of inositol in conjunction with the first composition. The inositol and magnesium may be administered simultaneously or sequentially in either order at the same or different times of day. In some embodiments, the first and second composition may be combined in a single pharmaceutical composition. The amount of inositol in the second composition may be increased by up to about 250 mg per day for 24 weeks (a third, fourth, fifth, sixth, seventh and eighth month), for a total of 18000 mg per day. Tolerance to inositol may be characterized by an absence or tolerable amount of nausea, tiredness, headache, and dizziness. In some embodiments, the second composition may be administered at an earlier time point, such as starting at the second month of treatment. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium and inositol combination. If it is determined that additional treatment is needed, the individual patient may further be administered a third composition comprising a third voltage dependent calcium channel antagonist such as about 500 to about 1000 mg of N-acetylcysteine per day in combination with the first and second composition for a ninth, tenth, eleventh and/or twelfth month or at an earlier time point such as at the fifth month, sixth, seventh and eighth month. Additionally, if mutually decided by all pertinent practitioners/providers and the patient, the individual patient may take a fourth composition comprising about 50 mg per day of zinc. The combination of the first, second, third and fourth compositions may be continued for a total of 24 months counting from the first administration of the first composition. The first, second, third and fourth compositions may be administered simultaneously or sequentially in either order at the same or different times of day. In some embodiments, the one or more of the first, second, third and fourth compositions may be combined in a single pharmaceutical composition. The individual patient may continue meeting with a mental health professional on a weekly basis for determination of changes in functions, reduction in signs and symptoms, lowered emotional pain, less over-reactive emotional responsiveness, less internalization and less guilt as well as tolerance of the magnesium, inositol, N-acetylcysteine combination and zinc combination.

These and other embodiments are more fully described in the Detailed Description section. It is to be understood, however, that there is no intention to limit the invention to the forms described in this Summary or in the Detailed Description. One skilled in the art can recognize that there are numerous modifications, equivalents and alternative constructions that fall within the spirit and scope of the invention as expressed in the claims.

DETAILED DESCRIPTION

Glossary

"Calmodulin" in this context refers to a multifunctional intermediate messenger protein that transduces calcium signals by binding calcium ions and then modifying its interactions with various target proteins.

"Languaging" in this context refers to a term coined by Swain (1985) relating to the cognitive process of negotiating and producing meaningful, comprehensible output as part of language learning.

DESCRIPTION

Described herein is a method of treating refractory Emotional Cognitive Disconnect (ECD). In some embodiments, such treatments will allow voltage dependent calcium channels (VDCCs) to function in a chronological sequence that connects the correct synapses together to process an experience and connect the emotions which are generally stimulated by experiences, situations, interactions, tasks, and/or memories. Cognitive thoughts may or may not match the emotions triggered. In further embodiments, the methods of treatment may return the structural system from a sympathetic nervous system reaction to a parasympathetic nervous system reaction. In additional embodiments, treatment of refractory ECD may be accomplished through the stabilizing of synaptic processing capacity and/or the lengthening of synaptic sequences. In other embodiments, treatment of refractory ECD may be accomplished through the inhibition of voltage dependent calcium channels (VDCCs).

VDCCs are specific regulatory and responsive small units within each individual neuron, and depending on the activation level from multiple sources, either facilitates, maintains or inhibits the flow of information from adjacent neurons and to adjacent neurons, as well as within each neuron, the next needful sequential processing unit until both the emotional information, particularly if negative, matches and connects with it. Initially the brain utilizes short term memory processing, and as the processing becomes complete it continues on to long term memory, at which point the emotions have been extracted and biochemicals metabolized to neutral so that in recalling the experience or interaction, little or no negative emotion remains. There are gender differences in this mechanism, in that males generally process negative emotion much quicker in a simpler set of sequences than do females. This is not pathological in nature; it is simply a result of different neurochemistry and needful pathways. Males being more linear, while female emotional processing has been described as pin-balling.

Experiences of both challenge and support assemble the synaptic pathways, first activating the VDCCs and then deactivating them in order to complete emotional processing, and the assembly of limbic/cortical connections, ECC. VDCCs can either be activated efficiently for maximum use of dendrite-axonal information processing, ECC. If not activated sufficiently, the information is not processed or not processed completely. VDCCs can also be over-activated which can deplete neuronal resources leading to pruning, atrophy, cell death or not being available for the next processing need, or ECD.

Regulating the biochemistry and re-regulating it back (if it does not reset normally) will enable the body to conserve its biochemical and nutritional resources per type of experience it has, instead of over-reacting and then depleting its own resources, which is what happens in anxiety and depressive disorders, and appears to be a major factor in dementias as well as other types of disorders. Achieving emotional cognitive connections (ECC) by preventing, arresting, reversing ECD increases normal calcium channel cascades, which reduces sympathetic over-arousal, allowing parasympathetic functioning to be achieved and maintained, thereby reducing oxidative stress, dysregulation of glutamate, reducing inflammation and inflammatory pathways, and reducing the usage of physical pain pathways by negative emotional overload (ECD). It also promotes glial cells to complete the ECC process and consolidate each new segment. It can also assist in reducing any negative effect of cholesterol metabolites. Enabling synaptic connections to connect emotional (limbic) system and cortical (cognitive/speech center) processing capacities to process experiences to completion resulting in emotional learning; and the evaporation of negative emotion.

Prolonged sympathetic arousal can lead to acidic biochemical environments in the body, which then leads to systemic compromise in vulnerable organs due to hypothalamic pituitary adrenal (HPA) Axis hormone release >4-5 (approximate) range of pH. Prolonged ECD affects neurotransmitters, in whatever order and sequencing that is unique to that individual. VDCCs begin to be affected intra-neuronally, which then affects all other biochemistry affected by the overwhelm or stress response. Specifically, major systems such as immune, cardiac, respiratory, etc. are affected. Once VDCCs are affected, then molecules, chirality, crystal structure and protein folding are affected. This, in turn, can affect gene transcription and expression. Under situations of not overwhelm, the brain can figure out how to move each emotional stimuli from dendrite to axon to dendrite to axon through to ECC completion. In situations of continuous overwhelm, such as in ECD, in order to decrease the stress response and return the major systems to normal, VDCCs must be inhibited.

In situations of ECD, once the VDCCs become involved and are functioning independently to process emotional reactions and cognitive thought; the separation of cognitions and emotional reactions, which occur respectively in the cortex and limbic system, becomes entrenched and stable, with each processing need consolidating the separation. When ECD moves quickly into emotion and cognition connect (ECC), due to sleep, eat, calm, and/or empathic emotional support then the acidic biochemistry reverts back to alkaline and the body resets itself, using the cascade regulatory feedback mechanism in a positive way.

This will look, feel, function and then begin more cascade reactions, when congruent. The process of experience→reaction→processing that includes both emotional and cognitive sequencing, that then allows the reactions to naturally resolve internal tension and negativity that was congruent with the experience into a neutral perspective, with emotional learning as a result. Individual growth results, as well as internal confidence, and connections with others that allow then, the reactions to be completed.

The treatment protocol described herein will assist the brain in building and stabilizing synaptic processing capacity by lengthening synaptic sequences, particularly for negative events and feelings, by inhibiting VDCCs to guide axons to next appropriate dendrite in order to create a linear emotional process, with cognitive (including speech) connections in order to complete the processing, remain parasympathetic, and both start and complete the greatest number of cascades to do so, while evaporating negative emotions in the process.

The goal is to maintain or restore parasympathetic functioning in the optimal band (the area between the parasympathetic nervous system and sympathetic nervous system) in order to ensure that intra-neuronal calcium channels operate sequentially per stimulus, dendrite to axon in order to ensure completion of synapse to synapse processing, with emotional-cognitive connections intact and stable.

In cases of ECD when the cognitive resources (synaptic pathway templates previously created and utilized) are not adequate to match the intensity, duration or frequency of emotional stimuli, usually sympathetically driven, then calcium channels require assistance in order to operate sequentially per stimuli, dendrite to axon in order to restore parasympathetic functioning and maintain it.

The regulation occurs in the intra-neuronal calcium channels specifically so that the osmotic pressure assists the channels to open and close on cue, which facilitates the ECC process sequentially, dendrite to axon, in order to utilize connecting pathway templates and prevents ECD. The exact biochemistry involves very specific movement from side to side, and specific coordination between these structures, in order for the functions to occur properly. When sequentially fired, the mechanisms connect and coordinate transmissions and ECC. Those mechanisms, which ECC is operating parasympathetically, all regulate calmodulin, which regulates the intra-neuronal calcium channels ensuring maintenance of ECC. Up to four calcium ions are bound by calmodulin via its four EF hand motifs. EF hands supply an electronegative environment for ion coordination. After calcium binding, hydrophobic methyl groups from methionine residues become exposed on the protein via conformational change. This presents hydrophobic surfaces, which can in turn bind to Basic Amphiphilic Helices (BAA helices) on the target protein. In rats, $Ca^{2+}$ plus calmodulin-stimulated reactions are maximally active in the range 30-50 mM $Mg^{2+}$, but the $Ca^{2+}$ plus calmodulin dependent phosphorylation of synapsin I are progressively inhibited by concentrations of $Mg^{2+}$ above 5 mM. It is currently believed that it is similarly important to achieve optimum Mg2+ concentrations in humans. Additionally, the N-methyl-D-aspartate (NMDA) glutamate receptor and ion channel protein in nerve cells, which is very important for controlling synaptic plasticity. NMDA's activation is voltage-dependent, a result of ion channel block by extracellular $Mg^{2+}$ and $Zn^2$. Magnesium-deficiency causes NMDA coupled calcium channels to be biased towards opening, causing neuronal injury and neurological dysfunction.

The sequential mechanisms operate automatically when parasympathetic and fire off the cascade regulatory feedback mechanism. When sympathetically driven, can experience ECD, which then leaves sequences unconnected, as well as create or at least allow feedback inhibition. If that pattern continues over time, then the calcium channels create a pathway template that resembles a less stable form of calcium carbonate, $CaCO_3$, most likely the aragonite form, which becomes rock-like over time in continuing to miss sequences and feedback inhibition. In the natural world, $CaCO_3$, whether calcite (the more stable version), or aragonite, is generally only resolvable (such as cave formation, stalactites, or stalagmites), using acidic liquids. The stability of the calcium-derived formation intra-neuronally means that it continues to be utilized and stabilized unless and until something more powerful than it is, changes. Possible change agents are the maturational process itself, change of environment so that sympathetic overarousal can reset back to parasympathetic, and stay there; empathically attuned social and emotional support, to supply new ways to view the problem or situation, which help the individual feel differently about the situation or problem, and to feel differently about themselves; and pharmaceutical agents. The two primary issues are reduction of internalized projection from others, which usually has taken the form of self-blame, guilt or self-criticism, and reduction in high anxiety or fear, which automatically result when there is a mismatch between the ability to think through a situation or problem and the intensity of negative feelings that are derived from it, leading to ECD.

Calcium is both stable as a solid, as well as soluble, depending on conditions and variables. If sympathetic arousal has dictated the synaptic pathways, rather than parasympathetic, then it becomes stable in an unstable manner. However, it can also be re-regulated to the correct parasympathetic pattern. The importance of $Ca^{2++}$ acts as an important second messenger, as a signal molecule within the cell itself, $Ca^{2++}$ is free and active and has a limited time frame within which to do its job. It is stored within organelles, such as the endoplasmic reticulum where it is bound to molecules like calreticulin. $Ca^{2++}$ has to be released from the ER into the cytosol, using the inositol 1, 4, 5-trisphosphate (InsP3) receptor and/or the ryanodine receptor. Levels of inositol have been reported to be decreased in cases of depression. In addition to its interaction with calcium, it is hypothesized that inositol may reverse desensitization of serotonin receptors.

The localized and time-limited activity of $Ca^{2++}$ in the cytosol is also called a $Ca^{2++}$ wave. This wave is built by the feedback mechanism of the ryanodine receptor and the activation of phospholipase C by $Ca^{2++}$, which leads to production of inositol troposphere, which in turn activated the InsP3 receptor. Calcium is necessary for neurotransmitter release, cytoskeleton management, cell migration, gene expression for specifics. One of the best-studied interactions of $Ca^{2++}$ with a protein is the regulation of calmodulin by $Ca^{2++}$. The specific location of the intervention is the optimal activation band located between the parasympathetic nervous system and the sympathetic nervous system (it has also been previously cited as the hypothalamus). Over time this will re-regulate the parasympathetic nervous system, which by nature operates in a sequential way to connect limbic-system experienced emotions with cortex-function, cognitive thought, which can then include receptive and/or expressive speech patterns, and behavior, if needed. Once the system is set-up, life experience (along with empathically-attuned emotional support) will maintain and stabilize it. In turn, as the individual moves along through life, parasympathetically-activated experiences will lengthen the pathways, as more and more connections creates more and more connections.

Biochemically it comes down to how one atom is placed in the benzene-ring type formation, and which chiral formation it creates in the process. Even one electron moving position can change the function of the resulting structure. The placement of the benzene-ring type formation, specifically in the ryanodine receptor, inositol (IP3), which regulates calmodulin, which then in turn regulates the calcium channels. Specifically, calmodulin controls neurotransmission, cell motility and other cellular mechanisms. Many of the $Ca^{2++}$ regulated processes are mediated through calmodulin, which serves as a major intracellular calcium ion receptor. The ionic form of $Ca^{2++}$ is active under physiological conditions because in the watery internal environment the calcium atoms gives up two electrons and then becomes a divalent cation. It is very stable. Kinetic evidence suggests that the binding of calcium ion proceeds sequentially and that calmodulin requires three or four bound calcium ions for activity. The entire reaction is reversible and under physiological conditions its direction is thought to be controlled by the cellular flux of calcium ions rather than the cellular concentration of calmodulin. Along with this, the specifically timed roles of sodium and potassium which altogether with calcium dictate the opening and closing of VDCCs and thus when and where and for how long calcium moves in and out of the calcium channel, which either facilitates synaptic transmissions or not. IP3 (mentioned above) a glucose isomer and second messenger precursor, is essential for several specific functions, nerve guidance, intracellular $Ca^{++}$ concentration control, in one study active in left superior temporal gyms, cell membrane potential maintenance, neurotransmitter activity modulation, gene expression. Understanding and controlling sympathetic arousal, the relationship to calcium channel function and this relationship to neurological malfunction, in this case, dementias in several forms, especially Alzheimer's, is crucial to slowing the deterioration, reversing the deterioration, and preventing it. A significant study recently published correlated calcium channel function with five major psychiatric disorders, with strong genetic implications. In addition, many studies have been published addressing various aspects of calcium channel dysregulation and the effect on neurological problems, or dementias in various forms. One of the risk factors associated with neurological dysregulations, dementias, is depression. Biochemical specifics of dementias, in particular Alzheimers's relate to abnormal insoluble amyloid protein fragments and neurofibrillory tangles that are intracellular disturbances in the microtubule complex. Overactivation of these neurons seems to allow calcium to continuously leak into the cell. Thus it appears that post-synaptic receptor sensitivity that is the problem, rather than excess release of glutamate. Several aspects of this problem have been identified, with several different approaches already in process. One specific remedial drug is Aricept, along with others.

At the psychological level, the role of empathic attunement in the interaction/relationship process has been identified as very significant in the development of ECC, while exposure to rejection, negative over-whelm, projection, lack of empathic attunement has also been identified as very significant in the development of ECD. The relationship of ECC and empathic attunement has been assumed and is currently being assumed as highly correlated with re-setting sympathetic reactions and functioning to parasympathetic, along with the assumption that lack of empathic attunement, rejection, projection (which is then internalized, sometimes situationally, often developmentally) is highly correlated with ECD.

Individuals may be diagnosed with refractory ECD by any means generally used by those of skill in the art. In some embodiments, diagnosis may occur through the use of clinical scales such as, but not limited to, the Beck Depression Inventory or the Cage Questionnaire for the Testing of Opioid Dependence of Sexual Abuse Victims with Chronic Pain both of which imply ECD clinically. In other embodiments, diagnosis may occur through clinical observation including observation of, but not limited to, (1) the defined separation of affect/emotion and cognition based on each individual; (2) the inability to self-observe the separation and account for it; (3) the inability to combine the various affects and cognitions by the individual; (4) the repeated inability of the individual to listen when affect/emotion and cognitions were combined by someone else; (5) the level of difficulty that the separate reactions caused in the individuals lives, both historically and current; and (6) the inability to not only combine what others combine easily and without obvious effort, followed by the subsequent inability to learn from past experiences in order to make the present and future different; (7) the inability to problem-solve and plan in sequential steps; (8) when combinations occurred, with great difficulty and much time delays, and repeated efforts, with someone else's assistance, with an initial cognitive and emotional reaction of positive, immediately followed by self-doubt, self-criticism, self-recrimination, that is, once Emotion and Cognition Connect (ECC) occurred, then negative thoughts and feelings were a result, rather than sustained positives; (9) Panic Disorder; (10) Panic Attacks; (11) some Phobic Reactions; and finally, (12) the beginning stages of some dementias, especially Alzheimer's. In further embodiments, diagnosis may be determined through patient complaints or family observations of problems with depression, anxiety, flashbacks, reenactments, self-sabotage as well as medical problems such as, but not limited to, headaches, stomachaches, muscle tenseness, difficulty with self-care behaviors, chronic pain, chronic back pain, or other indicators known to those of skill in the art. In additional embodiments, diagnosis of ECD may occur through a combination of one or more of clinical scales, clinical observation, patient complaints and family observations.

The amount, timing and mode of delivery of compositions for the treatment of ECD comprising an effective amount of the treatment protocol will be routinely adjusted on an individual basis, depending on such factors as weight, age, gender, and condition of the individual, the acuteness of the targeted disorder and/or related symptoms, whether the administration is prophylactic or therapeutic, and on the basis of other factors known to effect drug delivery, absorption, and pharmacokinetics, including half-life, and efficacy.

Effective unit dosage amounts of either or both of the pharmacological and alternative treatment options may be administered in a single dose, or in the form of multiple daily, weekly or monthly doses, for example in a dosing regimen comprising from 1 to 5, or 2-3, doses administered per day, per week, or per month. In exemplary embodiments, exemplary dosages of selected compounds are administered one, two, three, or four times per day. In more detailed embodiments, specific dosages within the specified exemplary ranges are administered once, twice, or three times daily. In alternate embodiments, dosages are calculated based on body weight, and may be administered, for example, in amounts as exemplified below adjusted for body weight.

Individuals diagnosed with Emotional Cognitive Disconnect are given a first composition comprising 250 mg of magnesium, taken once daily for about four to about eight weeks, with weekly check-ins with provider. The individual may meet weekly with a therapist or other mental health professional once a week for the about four to about eight weeks for assessment of tolerance to the magnesium and/or increased emotional processing. Tolerance may be determined by an absence of stomach upset, nausea, vomiting, or diarrhea. Those skilled in the art will know that a clinician will during the period observe patient interaction styles, ask patient for any observations their family has made, observe their facial expressions, observe their body language, observe their ability to language experiences they may report, and carefully document all these plus any other observations. Ask the patient if they think this treatment so far is helping them. Observe carefully for any negative reactions or responses, and evaluate them for validity and congruence with other information. It is imperative that the family of the patient be interviewed as well, at every point along the way, after their historical accuracy has been substantiated, and that accurate information be included in evaluating the treatment regime and decide what direction next to proceed. Sometimes the providers opinion should be the deciding factor, having said that, it is also true that at times provider's misinterpret the patterns for seriousness of the problem, as well as improvements, or not improvements. All results need to be carefully analyzed over time for internal integrity.

Once the patient has stabilized on that dose of magnesium, if more remediation is needed as evaluated after about four to about eight weeks, as determined by the patient, the practitioner and/or both, the patient is then placed on inositol, 250 mg. per day up to 18000 mg. per day for 12-48 weeks making sure that patient can tolerate this product, then weekly check-in with the patient, as above, their observations as well as clinician observations about changes in functions, reduction in signs and symptoms and lowered pain. Also less over-reactive emotional responsiveness, less internalization, less guilt, increased functionality. Also observing from same perspectives in Step 2 and 3, again documenting all observations carefully. In some embodiments, the inositol may be increased about 250 mg per day. In other embodiments, the inositol may be increased by greater or lesser amounts until 18000 mg is reached.

As patient maintains on magnesium and inositol, tolerated well, and signs and symptoms are lowered, and maintained at the lowered level, as indicated by a lowered sympathetic response overall, if more intervention is needed, add N-acetylcysteine, 500 mg. to 1000 mg. per/day for 4-20 weeks. N-acetylcysteine is a hepatoprotective antioxidant that is converted to cysteine, a substrate for the glutamate-cysteine antiporter. This antiporter allows for the uptake of cysteine, which causes the reverse transport of glutamate into the extracellular space, which stimulates inhibitory metabotropic glutamate receptors and, thereby, reduces synaptic release of glutamate. The restoration of the extracellular glutamate concentration in the nucleus accumbens seems to block reinstitution of compulsive behaviors.

If further treatment is indicated, Applicant's invention includes having the patient continue taking all three products, continue evaluating weekly, then bi-weekly followed by monthly for 3-6 months. If the patient is also being treated clinically by a psychologist, collaborate with their data to consolidate the treatment efforts. Specifically, the psychologist or other mental health processional can provide both reported data as well as observational data about how patient is coping with life circumstances, their own emotions in addition to all observations by the clinicians. Along with reduction in signs and symptoms originally observed and documented, determine that sympathetic arousal is gradually shifting to parasympathetic arousal. These products can be used for up to 24 months as needed or longer.

ECD indicators unstabilized by existing protocols for a compromised immune system include the following additional measures. If mutually decided by all pertinent practitioners involved/providers, family of patient, and patient, the treatment may further include 2000 units of vitamin E per day for 52-104 weeks. The treatment may additionally include the administration of 2000 mg of vitamin C per day for 52-104 weeks in combination with the vitamin E. Further treatment protocols include 2000 units of vitamin E, 2000 mg of vitamin C and 50 mg of zinc per day for 52-104 weeks. Applicant's treatment can further include the steps of continuing to administer 2000 units of vitamin E, 2000 mg of vitamin C and 50 mg of zinc per day, and also administer 5000 mcg. of Biotin per day for 52-104 weeks. Applicant's treatment can further include the steps of continuing to administer 2000 units of vitamin E, 2000 mg of vitamin C and 50 mg of zinc per day, 5000 mcg. of Biotin per day for 52-104 weeks, and adding 50 mg of alphalipoic acid twice a day, for 52-104 weeks. Finally, treatment may include 2000 units of vitamin E, 2000 mg of vitamin C, 50 mg of zinc per day, 5000 mcg. of Biotin per day and 50 mg alphalipoic acid twice day along with 1000 mg of lysine per day, for 52-104 weeks. The vitamin E, vitamin C, zinc, biotin, alphalipoic acid and lysine may each be administered alone or in combination with one or more of the other vitamins, coenzymes, antioxidants, amino acids and/or supplements included above.

These interventions are best augmented by psychological treatment focusing on guilt reduction, reduction in negativity, reduction in incompleteness, connecting emotions and emotions with through, and overall awareness of how the connections feel and what it means, followed by what to do about it. Increasing functionality will also be a focus of treatment.

Efficacy of the methods described herein will often be determined by clinical observation as well as the use of conventional patient surveys or clinical scales to measure clinical indices of ECD in subjects. The methods and compositions described herein will yield a reduction in one or more levels, scores or selected values generated from such measurements, surveys or scales completed by test subjects (indicating for example an incidence or severity of ECD), by at least 10%, 20%, 30%, 50% or greater, up to a 75-90%, or 95% compared to correlative scores or values observed for control subjects treated with placebo or other suitable control treatment. In at risk populations, the methods and compositions of the invention will yield a stable or minimally variable change in one or more levels, scores or selected values generated from such surveys or scales completed by subjects.

Increased parasympathetic functioning may be assessed using methods known to those skilled in the art including, but not limited to, a Valsalva maneuver, respiratory arrhythmia, isometric handgrip test, cold pressor test, mental arithmetic, orthostatic test, mental arithmetic test, head up tilt test, baroreflex sensitivity testing, analysis of heart rate variability, measurements of noradrenaline concentration, microneurography, thermoregulatory sweat test, sympathetic skin response and quantitative sudomotor axon reflex test. In other embodiments, parasympathetic functioning may be evaluated through clinical observation. In further embodiments, parasympathetic functioning may be evaluated using a clinical scale such as, but not limited to, the Beck Depression Inventory, or the Cage Questionnaire for the testing of Opioid Dependence of Sexual Abuse Victims with Chronic Pain. In additional embodiments, parasympathetic functioning may be evaluated using one or more of the tests, observations, and/or clinical scales alone or in combination. The methods and compositions described herein will yield a reduction in one or more levels, scores or selected values generated from such measurements, surveys or scales completed by test subjects (indicating for example an incidence or severity of ECD), by at least 10%, 20%, 30%, 50% or greater, up to a 75-90%, or 95% compared to correlative scores or values observed for control subjects treated with placebo or other suitable control treatment. In at risk populations, the methods and compositions of the invention will yield a stable or minimally variable change in one or more levels, scores or selected values generated from such surveys or scales completed by subjects.

Those skilled in the art will recognize that numerous modifications may be made to the preferred embodiment without departing from the scope of the claimed invention. It will, of course, be understood that modifications of the invention, in its various aspects, will be apparent to those skilled in the art, some being apparent only after study, other being matters of routine mechanical, chemical and electronic design. No single feature, function, or property of the preferred embodiment is essential. Other embodiments are possible, their specific designs depending upon the particular application. As such, the scope of the invention should not be limited by the particular embodiments described but should be defined only by the appended claims and equivalents thereof.

The invention claimed is:

1. A method of treating Emotional Cognitive Disconnect in treatment-resistant individuals, comprising:
   identifying an individual suffering from Emotional Cognitive Disconnect, wherein an individual presenting with:
   separation of affect/emotion and cognition,
   inability to self-observe the separation and account for it,
   inability to combine affects and cognitions, and
   repeated inability of the individual to listen when affect/emotion and cognitions are combined by someone else,
   is identified as suffering from Emotional Cognitive Disconnect;
   administering daily to the individual a first composition consisting of 250 mg of magnesium per day for a first month;
   evaluating the individual weekly for tolerance of the first composition;
   monitoring the individual weekly for increased emotional processing, wherein increased emotional processing is a decrease in the separation of affect/emotion and cognition;
   determining the tolerance for the first composition; and
   while continuing administration of the first composition, sequentially administering daily a second composition comprising about 250 mg of inositol, wherein a level of inositol is increased by about 250 mg per day for a second, third, and fourth month.

2. The method of claim 1, wherein the inositol is increased to about 18000 mg per day.

3. The method of claim 1, further comprising sequential daily administration of a third composition comprising about 500 mg to about 1000 mg per day of N-acetylcysteine in combination with the first composition and the second composition for a fifth and sixth month.

4. The method of claim 3, further comprising sequential administration of a fourth composition comprising about 50 mg of zinc.

5. The method of claim 4, wherein the first, second, third, and fourth compositions are administered up to a total of 24 months.

6. The method of claim 1, wherein the individual is evaluated by clinical observation.

7. The method of claim 1, wherein tolerance for the first composition is determined by an absence of stomach upset, nausea, vomiting, or diarrhea.

8. A method of restoring parasympathetic functioning comprising:
   identifying an individual suffering from Emotional Cognitive Disconnect, wherein an individual presenting with:
   separation of affect/emotion and cognition,
   inability to self-observe the separation and account for it,
   inability to combine affects and cognitions, and
   repeated inability of the individual to listen when affect/emotion and cognitions are combined by someone else,
   is identified as suffering from Emotional Cognitive Disconnect;
   administering daily to the individual in need of restoration a first composition consisting of 250 mg of magnesium for a first month;
   evaluating the individual weekly for tolerance of the first composition;

monitoring the individual weekly for increased parasympathetic functioning;

determining the tolerance for the first composition; and while continuing administration of the first composition, sequentially administering daily a second composition comprising about 250 mg of inositol, wherein a level of inositol is increased by about 250 mg per day for a second, third, and fourth month.

9. The method of claim 8, wherein the inositol is increased to about 18000 mg per day.

10. The method of claim 8, wherein increased parasympathetic functioning is evaluated using one or more methods selected from a Valsalva maneuver, respiratory arrhythmia, isometric handgrip test, cold pressor test, mental arithmetic, orthostatic test, mental arithmetic test, head up tilt test, baroreflex sensitivity testing, analysis of heart rate variability, measurements of noradrenaline concentration, microneurography, thermoregulatory sweat test, sympathetic skin response, and quantitative sudomotor axon reflex test.

11. The method of claim 10, further comprising sequential daily administration of a third composition comprising about 500 mg to about 1000 mg per day of N-acetylcysteine in combination with the first composition and the second composition for a fifth and sixth month.

12. The method of claim 11, further comprising sequential administration of a fourth composition comprising about 50 mg of zinc.

13. The method of claim 12, wherein the first, second, third, and fourth compositions are administered up to a total of 24 months.

14. The method of claim 13, wherein the individual is monitored by clinical observation and by using at least one clinical scale selected from a Beck Depression Inventory, or a Cage Questionnaire for the testing of Opioid Dependence of Sexual Abuse victims with chronic pain.

\* \* \* \* \*